(12) United States Patent
Prohaska et al.

(10) Patent No.: US 7,422,646 B2
(45) Date of Patent: Sep. 9, 2008

(54) ELECTROCHEMICAL SENSOR WITH DRY IONOMER MEMBRANE AND METHOD FOR MAKING THE SAME

(75) Inventors: Otto J. Prohaska, Seymour, CT (US); Avinash Dalmia, Hamden, CT (US)

(73) Assignee: PerkinElmer LAS, Inc., Boston, MA (US)

( * ) Notice: Subject to any disclaimer, the term of this patent is extended or adjusted under 35 U.S.C. 154(b) by 106 days.

(21) Appl. No.: 10/029,659

(22) Filed: Oct. 22, 2001

(65) Prior Publication Data

US 2003/0085125 A1 May 8, 2003

(51) Int. Cl.
 *G01N 27/407* (2006.01)
(52) U.S. Cl. .................................. 156/60; 204/424
(58) Field of Classification Search .......... 204/421–429, 204/415; 156/60
 See application file for complete search history.

(56) References Cited

U.S. PATENT DOCUMENTS

| | | | |
|---|---|---|---|
| 3,055,759 A * | 9/1962 | Busby et al. | |
| 3,211,638 A * | 10/1965 | Halvorsen | |
| 4,171,253 A | 10/1979 | Nolan et al. | |
| 4,272,353 A * | 6/1981 | Lawrance et al. | 204/283 |
| 4,812,221 A * | 3/1989 | Madou et al. | |
| 4,820,386 A * | 4/1989 | LaConti et al. | |
| 4,879,005 A * | 11/1989 | Fray et al. | 205/794.5 |
| 4,900,405 A * | 2/1990 | Otagawa et al. | |
| 4,925,544 A | 5/1990 | Goldring | |
| 5,082,550 A | 1/1992 | Rishpon et al. | |
| 5,273,640 A | 12/1993 | Kusanagi et al. | |
| 5,302,274 A * | 4/1994 | Tomantschger et al. | |
| 5,322,602 A | 6/1994 | Razaq | |
| 5,527,446 A * | 6/1996 | Kosek et al. | |

(Continued)

FOREIGN PATENT DOCUMENTS

EP    0 325 562    1/1989

(Continued)

OTHER PUBLICATIONS

Beech et al, Carbon Monoxide Sensors, Electrochemistry at Loughborough, pp. 1-4, 1999.*

(Continued)

*Primary Examiner*—Kaj K Olsen
(74) *Attorney, Agent, or Firm*—St. Onge Steward Johnston & Reens LLC

(57) ABSTRACT

A miniaturized gas sensor comprised of film type electrodes, on a non-conductive supportive substrate, and in contact with a dry ionomer electrolyte, for detection of toxic gases, i.e., carbon monoxide, and other oxidizable or reducible gases and vapors and method of making same is described. The all-solid planar sensor cell has two or more film type electrodes arranged on a non-conductive planar surface of a supportive substrate. Manufacturing the electrochemical sensor with dry ionomer prevents electrode flooding and allows for improved response time upon assembly. The sensor cell contains no liquid electrolyte and is operated in a constant-voltage, potentiostatic or potentiodynamic mode. A high sensitivity to a select gas or vapor is achieved by a three-phase contact area design for a sensing electrode, which provides contact with the solid ionomer electrolyte, as well as the gas sample via diffusion openings or holes that penetrate through the supportive substrate.

12 Claims, 9 Drawing Sheets

U.S. PATENT DOCUMENTS

| | | | |
|---|---|---|---|
| 5,547,551 A * | 8/1996 | Bahar et al. | 204/296 |
| 5,650,054 A * | 7/1997 | Shen et al. | 204/412 |
| 5,716,506 A | 2/1998 | Maclay et al. | |
| 5,746,899 A | 5/1998 | Finbow et al. | |
| 6,319,293 B1 * | 11/2001 | Debe et al. | 29/623.3 |
| 6,682,638 B1 * | 1/2004 | Prohaska et al. | 204/426 |
| 2001/0050230 A1 * | 12/2001 | Surampudi et al. | 204/422 |

FOREIGN PATENT DOCUMENTS

| | | |
|---|---|---|
| EP | 1 037 041 A2 * | 9/2000 |
| WO | WO 01/36957 A1 * | 5/2001 |

OTHER PUBLICATIONS

Encyclopedia of Polymer Science and Engineering, vol. 8, Wiley-Interscience, pp. 398 and 399, 1987.*

Aldrich Handbook of Fine Chemicals and Laboratory Equipment, 2003-2004, p. 1315.*

P.D. van der Wal, et. al, "Extremely stable Nafion based carbon monoxide sensor", Sensors and Actuators B, Elsevier Sequoia S.A., Lausanne, CH, vol. 35, No. 1, Sep. 1, 1996, 119-123.

* cited by examiner

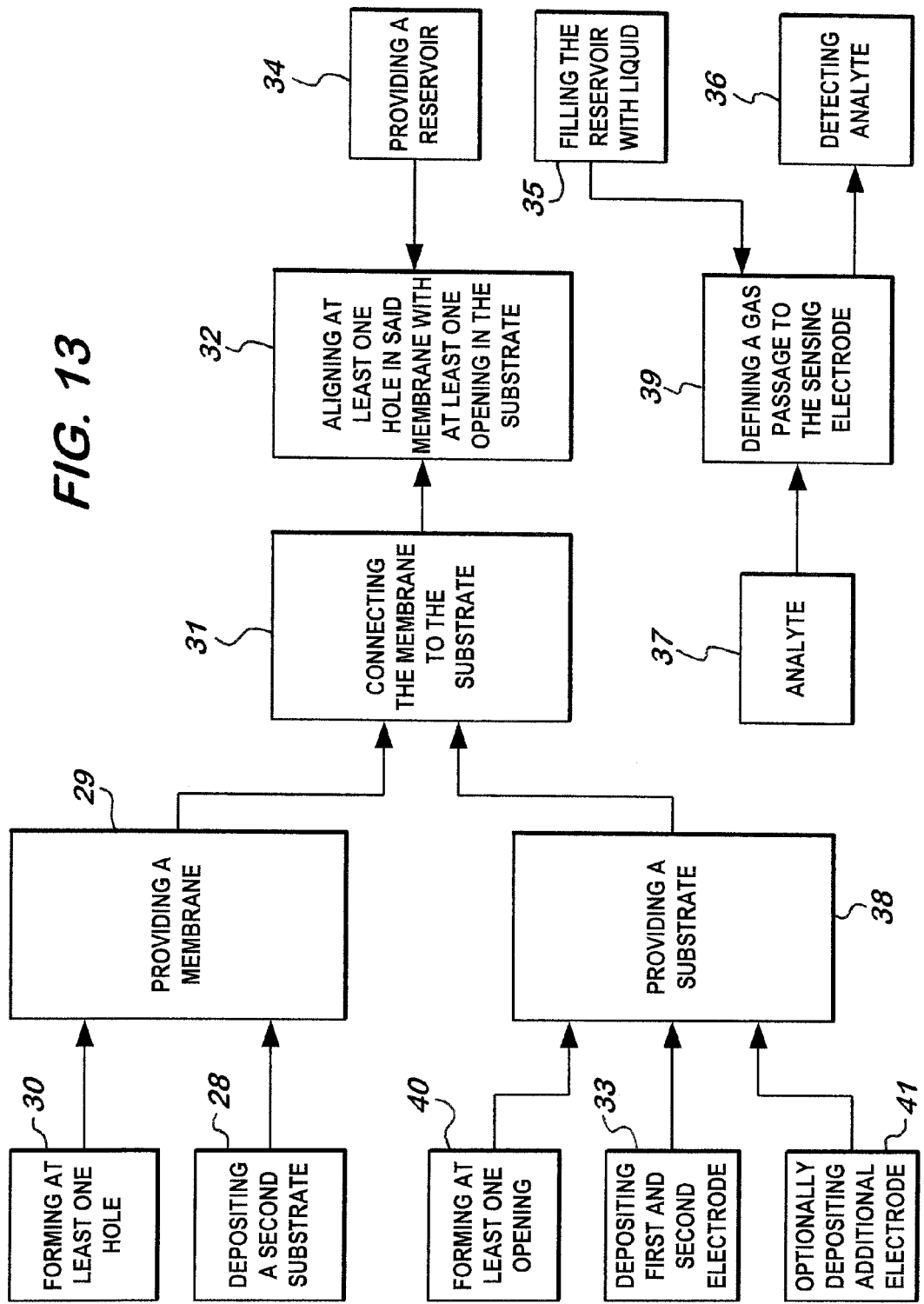

ELECTROCHEMICAL SENSOR WITH DRY IONOMER MEMBRANE AND METHOD FOR MAKING THE SAME

FIELD OF THE INVENTION

The invention is directed toward an electrochemical sensor manufactured using a dry ionomer membrane, and a method of manufacturing the same.

BACKGROUND OF THE INVENTION

Solid, ionic conductive elements are known and have been used in hydrogen-oxygen fuel cells, as is well known to those skilled in the fuel cell art. The use of such solid, ionic conductive electrolyte elements in an electrochemical gas sensor has also been demonstrated, however, has not been heretofore proposed or used in such electrochemical gas sensors to solve the problems of electrode flooding in the typical prior art gas sensor, as we presently understand the prior art.

The present invention provides an improved, less expensive and simpler construction for an electrochemical gas sensor as well as a simplified operation without the prior problems of flooding the electrodes caused by the use of wet ionomer membrane or resins during fabrication. The electrochemical gas-sensing cell of the present invention is capable of sensing concentrations of electrochemically active gases in gas mixtures in the parts per billion range. The use of a dry ionomer membrane in the gas sensor fabrication eliminates the problem of flooding of the electrode surface in sensors manufactured utilizing a wet or pre-equilibrated ionomer membrane. The present invention utilizes a solid dry ionomer membrane to manufacture an electrochemical sensor. At a desired time after assembly, the ionomer membrane can be equilibrated with water so that the membrane obtains significant ionic conductivity at room temperatures. By postponing hydration of the ionomer membrane, calibration time of electrochemical sensors is unexpectedly reduced. The dry ionomer membrane can be utilized with film-based techniques, which have been widely investigated in electrochemical sensor microfabrication technology.

Film based techniques in microfabrication technology are known for a wide variety of sensors. Solid-state gas sensors have demonstrated the advantage of being able to operate at elevated temperatures, however they have the disadvantages of slow response and recovery time and a high internal operating temperature. The disadvantages and limitations of the state-of-the-art sensors prevent efficient usage of such sensors in battery-powered instruments.

Nafion®-coated metal oxide pH sensor with sputtered iridium oxide sensing and silver/silver chloride reference electrodes on alumina ceramic substrates are also known in the art. Nafion® has been used as a cation-selective ionomer coating in order to decrease the oxidation-reduction error generally affecting the performance of metal oxide pH electrodes. The use of Nafion® as polymer-electrolyte for a thin-film CO sensor with macro-sized, sputtered Pt sensing and counter electrodes and a smaller, sputtered Au electrode as reference electrode is also known in the art. A 5 wt % n-propyl alcohol solution of Nafion® (DuPont, 1100 EW) is used to form the polymer electrolyte film over the electrodes by casting. The polymer is washed and protonated in aqueous sulfuric acid prior to casting. The reported lifetime of this sensor is reported to be less than one month. During this time, the CO oxidation current decreases steadily down to a few percent of its original value without any period of stable measurement signal. The lifetime of the device may be extended up to three years by laminating the polymer electrolyte layer with a cast perfluorocycloether-polymer film in order to keep the CO permeability coefficient through Nafion® constant; theoretical calculations showed that the drift rate of the signal could be significantly reduced under these conditions.

Nafion® is a copolymer of perfluoro-3,6-dioxa-4-methyl-7octene-sulfonic acid and tetrafluoroethylene (Teflon). Nafion® can be described as having a Teflon backbone with occasional side chains added of another fluorocarbon. The side chain terminates in a sulfonic acid ($-SO_3H$). With the exception of the sulfonic acid group, all of Nafion® is a fluorocarbon polymer. Like most fluoropolymers, it is extremely resistant to chemical attack (corrosion resistant). The sulfonic acid group is immobilized within the bulk fluorocarbon matrix and cannot be removed, but unlike the fluorocarbon matrix the sulfonic acid groups do participate in chemical reactions. The presence of the sulfonic acid adds three important properties to Nafion®: 1) Nation® functions as an acid catalyst due to the strongly acid properties of the sulfonic acid group; 2) Nafion® functions as an ion exchange resin when exposed to solutions; 3) Nafion® very readily absorbs water, from the vapor phase or from the liquid phase. Each sulfonic acid group will absorb up to 13 molecules of water. The sulfonic acid groups form ionic channels through the bulk hydrophobic polymer, and water is very readily transported through these channels. Nafion® functions like a very selective, semi-permeable membrane to water vapor.

The physical properties of Nafion® are similar to other fluoropolymers. It is a translucent plastic, with reasonable flexibility. When used as an ion exchange membrane, it is specified by its manufacturer, DuPont, to operate at temperatures up to 190° C. An unusual property of Nafion® is its propensity to change in physical size. As Nafion® absorbs water, it will swell (increase in size) by up to 22%. When exposed to alcohols it will swell up to 88%.

Table 1 shows readily available types of Nafion® membranes. All measurements were taken with membranes conditioned to 23° C., and 50% Relative Humidity (RH).

| Membrane Type   | Nominal Thickness (mm) | Weight Caliper (g/dm$^2$) |
| --------------- | ---------------------- | ------------------------- |
| N-111           | 0025                   | 0.5                       |
| N-112           | 0.051                  | 1.0                       |
| N-1135, N-1035  | 0.089                  | 1.9                       |
| N-115, N-105    | 0.127                  | 2.5                       |
| N-117           | 0.183                  | 3.6                       |

Dry ionomer membranes can also be defined as those ionomer membranes that are hygroscopic. Hygroscopic membranes are those membranes that readily absorb or attract moisture from the air; or membranes having an affinity for moisture. One such example is Nafion® 117 perflourinated membrane manufactured and sold by E. I. du Pont de Nemours and Co. Dry ionomer membranes do not include membranes that have been soaked in any solution such as water, or acidic solution.

The present invention relates to the manufacture of electrochemical sensors using hygroscopic Nafion®, or Nafion® sold in dry sheets to form the ionomer membrane, which has had the unexpected result of facilitating the manufacturing process and the development of sensors with improved start-up times after assembly of the sensor.

Table 2 compares mechanical and electrical properties of dry sheet Nafion® at 50% RH and 23° C. to wet Nafion® soaked in water.

| NAFION ® Mechanical and Electrical Properties | | |
|---|---|---|
| Property | Typical Value | Test Method |
| Tensile Modulus, MPa (kpsi) | | |
| 50% RH, 23 C. | 249 (36) | ASTM D 882 |
| water soaked, 23 C. | 114 (16) | |
| water soaked, 100 C. | 64 (9.4) | |
| Tensile Strength (max), MPa (kpsi) | | |
| 50% RH, 23 C. | 43 (6.2) in MD, 32 (4.6) in TD | ASTM D 882 |
| water soaked, 23 C. | 34 (4.9) in MD, 26 (3.8) in TD | |
| water soaked, 100 C. | 25 (3.6) in MD, 24 (3.5) in TD | |
| Elongation at Break, % | | |
| 50% RH, 23 C. | 225 in MD, 310 in TD | ASTM D 882 |
| water soaked, 23 C. | 200 in MD, 275 in TD | |
| water soaked, 100 C. | 180 in MD, 240 in TD | |
| Tear Resistance - Initial, g/mm | | |
| 50% RH, 23 C. | 6000 in MD, TD | ASTM D 10004 |
| water soaked, 23 C. | 3500 in MD, TD | |
| water soaked, 100 C. | 3000 in MD, TD | |
| Tear Resistance - Propagating, g/mm | | |
| 50% RH, 23 C. | >100 in MD, >150 in TD | ASTM D 1922 |
| water soaked, 23 C. | 92 in MD, 104 in TD | |
| water soaked, 100 C. | 74 in MD, 85 in TD | |
| Density, g/cm$^3$ | 2.0 | — |
| Conductivity, S/cm | 0.083 | |

Table 2 shows that tear resistance (g/mm) of dry membrane increases with thickness. These values for tear resistance are typical of N-112 0.051 mm membrane.

Where specified in table 2, "MD" means machine direction, and "TD" means transverse direction. Also, conductivity measurements made for 1100 EW membranes utilizing membrane conditioned at 100 C water for 1 hour. The conductivity measurement cell was submersed in 25 C water during experiment, and membrane impedance (real) taken at zero imaginary impedance.

Table 4 compares water uptake from dry Nafion® membrane (dry weight basis) to water soaked Nafion® membrane at 100° C. for 1 hour.

| NAFION ® Hydrolytic Properties | | |
|---|---|---|
| Property | Typical Value | Test Method |
| Water Uptake, % water | 35 | ASTM D 570 |
| Thickness Change, % Increase | | |
| from 50% RH, 23 C. to water soaked, 23 C. | 10% | ASTM D 756 |
| from 50% RH, 23 C. to water soaked, 100 C. | 14% | |
| Linear Expansion, % Increase | | |
| from 50% RH, 23 C. to water soaked, 23 C. | 10% | ASTM D 756 |
| from 50% RH, 23 C. to water soaked, 100 C. | 15% | |

A description of typical state-of-the-art hydrated solid polymer electrolyte or ionomer sensors and sensor cells is described by Kosek et al. U.S. Pat. No. 5,527,446; LaConti and Griffith, U.S. Pat. No. 4,820,386; Shen et al., U.S. Pat. No. 5,573,648; and, Stetter and Pan, U.S. Pat. No. 5,331,310 all of which are herein incorporated by reference. These sensor cells, based on hydrated solid polymer electrolyte or ionomer technology, have several advantages over conventional electrochemical sensor cells. The catalytic electrodes are bonded directly to both sides of a proton conducting solid polymer ionomer membrane providing a stable electrode to electrolyte interface. One side of the electrolyte membrane is flooded with distilled water, making the sensor cell self-humidifying and independent of external humidity. Since no corrosive acids or bases are used in the sensor cell, a lifetime of over 10 years has been demonstrated for solid polymer ionomer sensor cells. Finally, the sensor cells are easy to maintain, and so are ideal for use in remote, unattended environments. Regular addition of water to the reservoir in the sensor housing every several months and monthly calibration checks are the only requirements.

One of the concerns with the state-of-the-art sensors described above is that the signal-to-noise ratio is not conducive to detection of very low concentrations (parts per billion, ppb) of important environmental and biomedical gases and vapors. Response time is relatively slow, and reproducibility between sensors and sensor cells is not high. Also, they are relatively costly.

Recently, miniaturized thick and thin film type sensors have been developed where the solid ionomer membrane acts as a conduit between the gas to be detected (sample gas) and the sensing electrode. The sample gas permeates through the membrane itself where a 3-phase contact area is established. The concern with this configuration is that the solid ionomer membrane water content controls the gas permeation rate as well as proton conductivity. As the humidity increases, the membrane water content increases. This causes an increase in the gas diffusion rate as well as proton conductivity and sensor signal response. The best method of controlling or fixing the water content of the membrane is to have a water reservoir on the back side of the membrane, directly opposite to where the film type electrodes and non-conductive supportive substrate are located, however other configurations positioning the water reservoir on the front side of the membrane are possible. Unfortunately in the back side configuration the back side of the membrane is required to be free of liquid so that the sample gas can diffuse through the membrane to the sensing electrode.

Another concern of the state-of-the-art sensors is flooding of the electrode surfaces caused during the fabrication of the sensors. Flooding causes the formation of liquid droplets on the electrode surface and results in decreased sensor sensitivity after assembly. Electrochemical sensor arrangements where an electrode lies immediately adjacent to a hydrated ionomer membrane are prone to flooding. The propensity to flood is further increased with the thickening of the electrode; hence thick film electrodes are more prone to flooding than thin film electrodes.

The propensity of electrode flooding is further increased by the common use of Nafion® as the ionomer membrane of choice. A perfluorosulfonic acid membrane is defined as a polymer that contains small proportions of sulfonic or carboxylic ion functional groups. Nafion® is typically cleaned extensively by boiling in water to remove impurities. The use of wet Nafion® in the manufacturing process results in the formation of liquid droplets on the electrode; hence sensors are formed with decreased sensitivity.

Typically, sensors with flooded electrodes need to be flushed with dry gas for extended periods greater than 24 hours in order to regain their optimal response rate. One typical embodiment of this invention solves the problems associated with wet Nafion® use by using a dry Nafion® sheet in the production process. This dry Nafion® sheet is obtained in hygroscopic form and has not been boiled, soaked in any liquid, or otherwise treated (i.e. equilibrated in an acidic solution).

The best method for hydrating the ionomer membrane such as Nafion® would be to have a water reservoir located adjacent to the membrane, and opposite to where the film type electrodes are located. These reservoirs can contain a water seal, which may be broken anytime after assembly in order to release water and hydrate the ionomer membrane. Providing an orifice in the sensor housing with a cap enables refillable reservoirs.

Another problem associated with the use of wet Nafion® in electrochemical sensors is that wet parts are difficult to work with. Therefore, making electrochemical sensors with dry Nafion® decreases the difficulty of handling materials during the manufacturing process.

Yet another problem associated with the use of wet Nafion® in the manufacturing of electrochemical sensors is that the wet parts may result in sensors with a varying amount of sensitivity from one another. Hence, using dry Nafion® provides a means of obtaining more uniform results in sensor reproducibility.

The present invention overcomes the limitations of the state-of-the-art in miniaturized electrochemical sensors stated above by uniquely combining a dry ionomer membrane configuration with a thick or thin film type electrode on a non-conductive supportive substrate. The substrate may have diffusion openings or holes having a known area, which permit easy access of the sample gas to a sensing electrode contact area. The sensor configuration provides a three phase contact area that serves as an interface for the ionomer membrane, the electrodes, and the gas being detected. This design utilizes the precision of solid-state device fabrication techniques to yield inexpensive, low maintenance, highly sensitive, rapidly responsive, and reproducible sensor devices for environmental, industrial, and biomedical monitoring.

SUMMARY OF THE INVENTION

This invention is directed toward a controllable and reproducible gas sensor configuration having a three-phase contact area, whereby the sample gas diffuses to the sensing electrode and membrane through openings, holes or slits that extend through the non-conductive supportive substrate.

This invention is further directed toward a gas sensor where the gas diffusion process is decoupled from the proton conduction process. The gas diffusion is controlled only through openings of known area in the substrate or in the substrate and an additional rate limiting gas diffusion barrier film or polymer layer, eg: polyethylene or Nafion® film, while proton conduction takes place only through an electrolyte layer, e.g., a Nafion® membrane. An important distinction to be made in this invention is that the gas diffusion barrier film or polymer layer may be manufactured using wet or dry Nafion® film, however, the novel Nafion® ionomer membrane must be dry hygroscopic Nafion® in order to effectively prevent flooding of the electrode.

The invention is also directed toward utilizing a method of mass-producing film type gas sensors by stacking a number of component layers to form a series of adjacent sensors which are subsequently separated into individual sensors.

The invention is still further directed toward a gas sensor utilized in conjunction with a gas sensor control circuit.

The invention is also directed toward a gas sensor utilized in a gas-sensing instrument.

The invention is still further directed toward a gas sensor that combines a dry form solid polymer ionomer membrane configuration with a thick or thin film type electrode on a non-conductive supportive substrate.

The invention is also directed toward a gas sensor where a few hours of storage time are required to make the sensor operational upon complete assembly.

The invention is still further directed toward a sensor with increased consistency in reproducibility of sensitivity levels within the manufacture of a batch of sensors.

The invention is still further directed towards manufacturing a sensor where upon completion of assembly the electrodes remain dry.

The invention is still directed towards a method for making electrochemical gas sensors by providing a dry ionomer membrane. This dry ionomer membrane may be Nafion®.

This invention is directed towards a method for making electrochemical sensors by providing a dry ionomer membrane, and a substrate that has holes through its surface and an electrode layer adjacent to the holes. Holes may be punched in the ionomer membrane so that the ionomer membrane can be mated to the substrate such that the holes of the ionomer membrane and holes in the substrate line up to form a gas inlet where the gas is able to contact the working electrode.

It is the object of the present invention to provide a method of making an electrochemical sensor for the detection of an analyte in a gas sample by providing a dry ionomer membrane free from liquid droplets; providing a substrate with at least one opening through its surface and a first electrode layer adjacent to the opening; connecting the dry ionomer membrane to the substrate; aligning the hole in the dry ionomer membrane with the opening in the substrate for defining a gas passage; and depositing a second electrode on the substrate for operatively connecting the ionomer membrane, the first electrode, the second electrode, and an analyte of interest. In certain embodiments, the dry ionomer membrane further includes a hole aligned with the sensing electrode for defining a gas passage.

It is the object of the present invention to provide a method of making an electrochemical sensor for the detection of an analyte in a gas sample by providing a dry ionomer membrane which is a dry sheet of Nafion®.

It is the object of the present invention to provide a method of making an electrochemical sensor for the detection of an analyte in a gas sample by making the sensor cell prior to wetting said dry ionomer membrane.

It is the object of the present invention to provide a method of making an electrochemical sensor for the detection of an analyte in a gas sample by positioning a polymer layer upon the sensing electrode for defining the diffusion rate at which the gas is moving through the inlet onto a surface of the sensing electrode.

It is the object of the present invention to provide a method of making an electrochemical sensor for the detection of an analyte in a gas sample wherein providing a substrate further includes positioning a counter electrode in contact with the dry ionomer membrane such that upon wetting the dry ionomer membrane the counter electrode provides an electrical connection to the ionomer membrane so current may be applied to said sensing electrode.

It is the object of the present invention to provide a method of making an electrochemical sensor for the detection of an analyte in a gas sample wherein the step of providing a substrate further includes positioning a reference electrode in contact with the dry ionomer membrane such that upon wetting the dry ionomer membrane a reference point is created against which the potential of other electrodes can be measured.

It is the object of the present invention to provide a method of making an electrochemical sensor for the detection of an analyte in a gas sample wherein the step of obtaining a dry ionomer membrane further includes obtaining a perfluorosulfonic acid membrane.

It is the object of the present invention to provide a method of making an electrochemical sensor for the detection of an analyte in a gas sample by providing a reservoir in contact with the dry ionomer membrane.

BRIEF DESCRIPTION OF THE DRAWINGS

FIG. 13 is a flow chart illustrating the manufacturing process for sensors of the present invention.

DETAILED DESCRIPTION OF THE INVENTION

Figure 1:
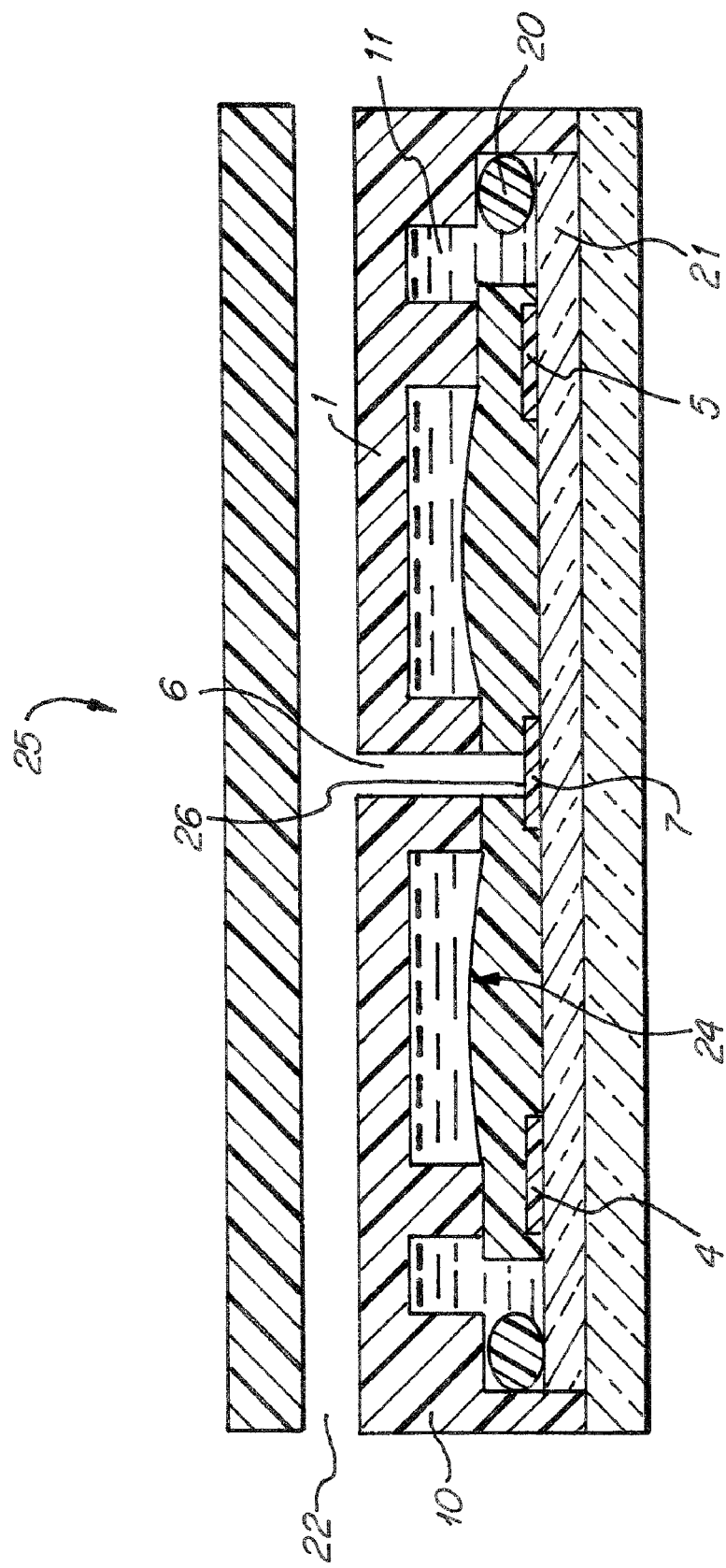
FIG. 1 shows a cross-sectional view in accordance with one preferred embodiment of the sensor cell assembly utilizing thick film type electrodes and a hole in the ionomer membrane.

FIG. 1 shows a cross-sectional view of one preferred embodiment of the sensor cell assembly (25). The sensor housing (10) contains a substrate (1) and sensor chip (21). The sensor chip is incorporated into the substrate so that it acts as a natural extension of the substrate upon assembly. A reference electrode (4), a counter electrode (5), and a sensing electrode (7) are disposed on the sensor chip (21). An ionomer membrane (24), i.e. Nafion®117 about 0.183 mm. thick, is positioned upon the sensor chip (21) so that it is in contact with each electrode and the substrate (1). A three phase contact area (26) is formed by gas inlet (6), i.e. of a circular shape, about 1.0 mm in diameter through the substrate (1) and ionomer membrane (24) immediately adjacent the sensing electrode (7). When a sample gas enters the housing at gas entrance (22) it travels to gas inlet (6), in order to pass through the substrate (1) and ionomer membrane (24). At which point the gas can enter a three-phase contact area (26) where it contacts the ionomer membrane (24) and the sensing electrode (7). Water reservoir (11) provides means for hydrating the dry ionomer membrane (24) after sensor assembly. Upon hydrating the ionomer membrane after assembly the sensor exhibits a fast response time because the ionomer membrane (24) acts as a proton-conducting element between the film type sensing electrode (7), reference (4), and counter electrode (5). In certain embodiments, hydrating ionomer membrane (24) after assembly prevents the problem of long calibration periods as found in the state-of-the-art electrochemical sensors due to flooding of electrodes (4), (5), and (7).

The sensor chip (21) can be made out of any material that one of ordinary skill in the art would use to make a sensor chip. For example, nonconductive examples of such materials include ceramic material, or glass. Sensor chip (21) is integrated and incorporated into the substrate such that it acts as an extension or continued piece of the substrate within the sensor housing (10). Water reservoirs (11) are positioned opposite the electrodes. In certain embodiments, the reservoirs contain a cap or seal that is desirably broken after the manufacture of the sensor so that water may hydrate the dry ionomer membrane (24). A reference electrode (4) and counter electrode (5) are positioned on the substrate such that they are in contact with the dry ionomer membrane (24), but are not in contact with one another or the sensing electrode (7). Each of the electrodes (4), (5), and (7) may each be manufactured out of platinum or of any material that one of ordinary skill in the art would use to manufacture thick or thin film type electrodes. This illustrates one preferred embodiment of the present invention. Other embodiments utilizing a two-electrode structure are certainly possible. Also, in certain embodiments, housing (10) includes an orifice or hole such that water reservoir (11) can be refilled with solution.

In FIG. 1, thick film type electrodes (4), (5) and (7) are deposited on a sensor chip (21). These electrodes may be arranged as one of skill in the art typically deposits electrodes on a substrates or sensor chips. For example, flag-type, dot-type, and band-type film embodiments known in the art are all possible.

Making the opening in the ionomer membrane can be performed by any method one of ordinary skill in the art would use to make a hole or slit in the membrane. For example, a simple punch apparatus may be used to punch a hole into a dry Nafion® sheet. Next, the punched ionomer sheet will be positioned on sensor chip (21) such that the punched holes are disposed on the sensing electrode (7).

Figure 2:
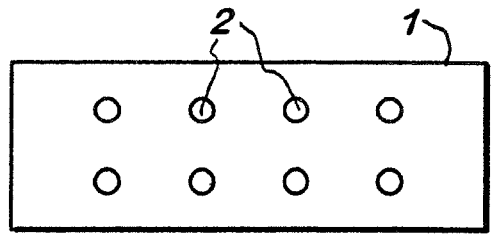
FIG. 2 shows a schematic top view of a non-conductive supportive substrate with openings in the substrate.

FIG. 2 shows the top view of another preferred embodiment of the invention having a ceramic film type substrate (1) (e.g., alumina) having holes (2) uniformly distributed in parallel rows. This embodiment relates to hybrid film type sensors. The distance between the holes in the parallel rows and the distance between the rows determine the dimensions of the sensor. The holes are ideally punched in a single step, while the alumina plate is still soft, in the "green" stage of substrate fabrication, prior to high-temperature sintering. Other techniques to create the holes include laser ablation or use of soluble fillers.

Figure 3:
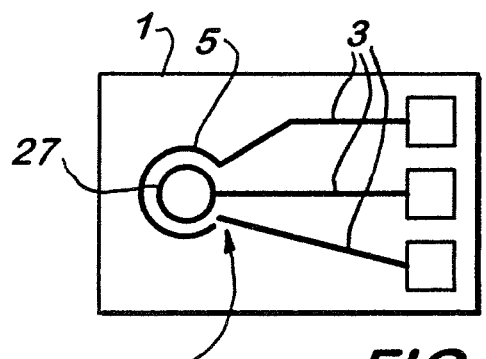
FIG. 3 shows a hybrid film type electrochemical sensor cell with Pt/Air ($O_2$) reference, and sensing and counter electrodes.

Using screen-printing or lithographic techniques, conducting leads (3) and thick- and thin-film electrodes are formed on the non-conductive substrate (1) for multiple electrodes. A typical hybrid sensor design utilizing this method is shown in FIG. 3, which has a single reference electrode (4) (e.g., Pt/Air ($O_2$) electrode) and a Pt counter electrode (5). The contact for the sensing electrode (27) is a ring concentric to the hole. This ring can be made of smooth, rough or platinized platinum. Some platinization may provide better contact. Simultaneous platinization of electrodes can be performed by customized electrolytic plating on properly masked multi-sensor plates.

The sensing or working electrode (7) may be a disc of Teflon®-bonded or Nafion®-bonded platinum or other electrocatalyst. In one preferred hybrid sensor embodiment a number of discs are deposited on an ionomer film, such as Nafion® electrolyte membrane (8) at uniform distances from each other, for instance, by decal transfer, silk printing, spray painting, artist brush lettering, or by any approach which lends itself to uniform deposition of a design on a transfer substrate without waste. The discs' distances from center to center are the same as for the holes of FIG. 2. The diameter of the sensing or working electrode disc is somewhat larger than the diameter of the hole in FIG. 2 to allow for contact between the disc and the sensing electrode support ring (27) of FIG. 3. Instead of a single large hole per sensor of FIG. 2 (which requires the use of the substrate to control diffusion of the analyte), a series of smaller openings may be used, with small enough diameters to control diffusion independently of the analyte flow. The areas of the openings are chosen so as to control diffusion of the sample gas toward the sensor and to maintain a constant diffusion rate independent of any changes in the sample gas flow rate. By using a number of these diffusion-controlling orifices, a reasonably large signal may be maintained.

Figure 4:
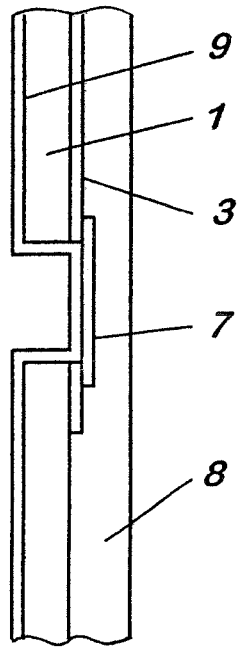
FIG. 4 shows a film type electrochemical sensor cell with a polymeric gas-diffusion layer over the sensing electrode membrane.

Over the empty alumina surface (the surface with no printed leads and electrodes) a gas-permeable diffusion film (9) is deposited in one configuration of the invention. This film is made to conform to the sensor electrode over the holes (as shown in FIG. 4), or hangs loose over the (sensor) sensing electrode (7). The substrate (with multiple arrays of printed conductors), the Nafion® membrane (with multiple sensing electrode discs), and the gas-permeable film are arranged as shown in the schematic representation of FIG. 4. After all the components are unitized, the resulting structure is cut in individual sensor units. This gas-permeable diffusion film (9) can also be disposed upon electrode (7) as shown in FIG. 1 as another embodiment of the present invention.

Figure 7:
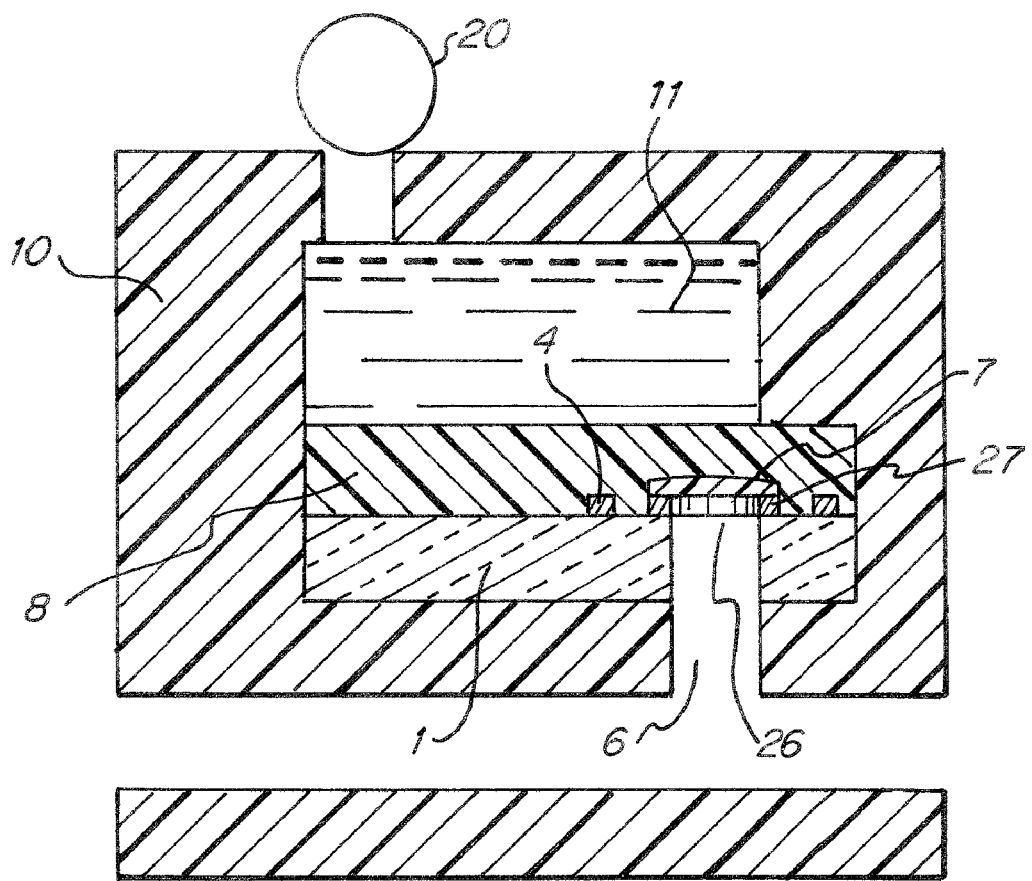
FIG. 7 shows a cross-sectional view of a hybrid sensor cell assembly.

An additional advantage of this structure as shown in FIG. (4) is that it allows for a water reservoir (11) over the Nafion® membrane (8) on the opposite, or back side from where the sensing electrode is located as shown in FIG. 7.

Figure 5:
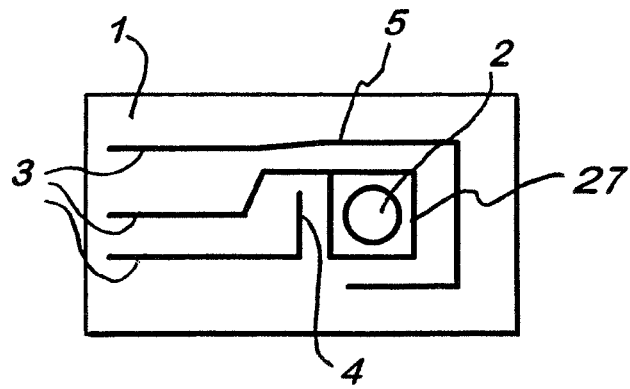
FIG. 5 shows a top view of a thick-film type electrochemical sensor cell.
Figure 6:
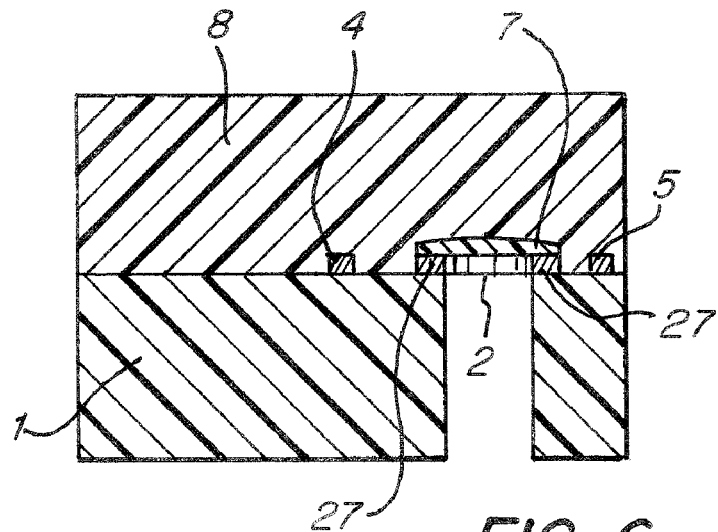
FIG. 6 shows a cross-section of the thick-film type electrochemical sensor cell.

A schematic drawing of the sensor cell assembly of this invention is shown in FIG. 5. In a preferred embodiment of this invention a hole of approximately 80 mils (0.080 in) is formed in a film type substrate (1) and sensing electrode contacts (27), and Pt counter (5) and reference electrodes (4) are then deposited on the substrate (1) surface as shown in FIG. 5. In an alternative embodiment of this invention the hole (2) is drilled directly through the non-conductive substrate and integral sensing electrode contact structure. As a result the sample gas has direct contact through the substrate hole (2) with the sensing electrode as shown in FIG. 6. This film type substrate structure is mounted in a sensor housing (10) as shown in FIG. 7 with a solid ionomer membrane (Nafion®117). The Pt sensing electrode support ring (27) (with hole in center) and solid counter (5) and reference (4) electrodes are compressed tightly against the Nafion® membrane (8). The fixture as shown in FIG. 7 has a water reservoir (11) on the opposite side of the membrane from where the electrodes are located. The reservoir (11) is filled with distilled water and wets the membrane, thus fixing and controlling the water content of the membrane and electrode assemblies. The reservoir (11) is sealed with a seal or cap (20).

The hybrid film type sensor configuration from above is integrated with a potentiostat and a voltage of approximately +0.1 V is applied to the Pt sensing electrode with respect to a Pt/Air ($O_2$) reference. This corresponds to an applied potentiostatic voltage of approximately 1.16 V with respect to a normal hydrogen electrode (NHE).

Gas samples of air and 7.4 ppm $SO_2$ in air are introduced into the sampling port of the fixture described above. The gas flow is approximately 60 $cm^3$/min and temperature is approximately 25° C. The sample gas diffuses through the 80-mil hole in the non-conductive substrate and electrochemically reacts at the exposed sensing electrode/solid ionomer electrolyte surface. Humidification is provided by the liquid water in the reservoir which soaks the opposite, or back side of the membrane as to where the electrode structures are located.

The background response signal with air is 30 nanoamps (nA). The response signal with 7.4 ppm $SO_2$ in air is 135 nA. This corresponds to a net response signal for 7.4 ppm $SO_2$ in air of 105 nA or 14.2 nA/ppm per 80-mil hole. It is possible to increase the magnitude of signal and signal-to-noise ratio by increasing the number of holes in the substrate above the integral sensing electrode structure.

It is also possible, with this configuration, to detect other oxidizable or reducible gases such as CO, NO, $NO_2$, $H_2S$, ozone, $CO_2$, hydrogen, hydrazine, ammonia, HCl, alcohols and acetone.

Figure 8:
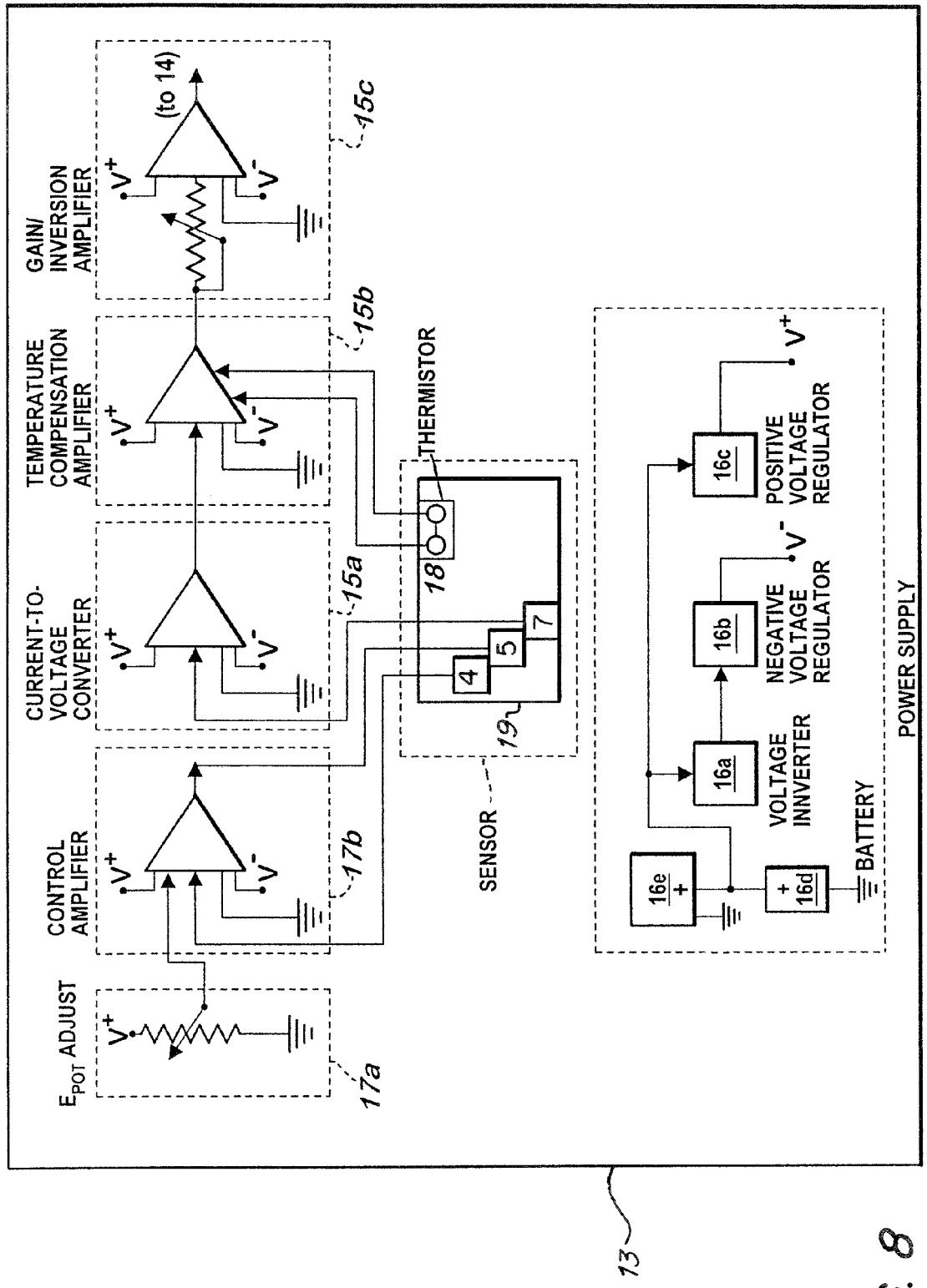
FIG. 8 shows a gas sensor control circuit.
Figure 9:
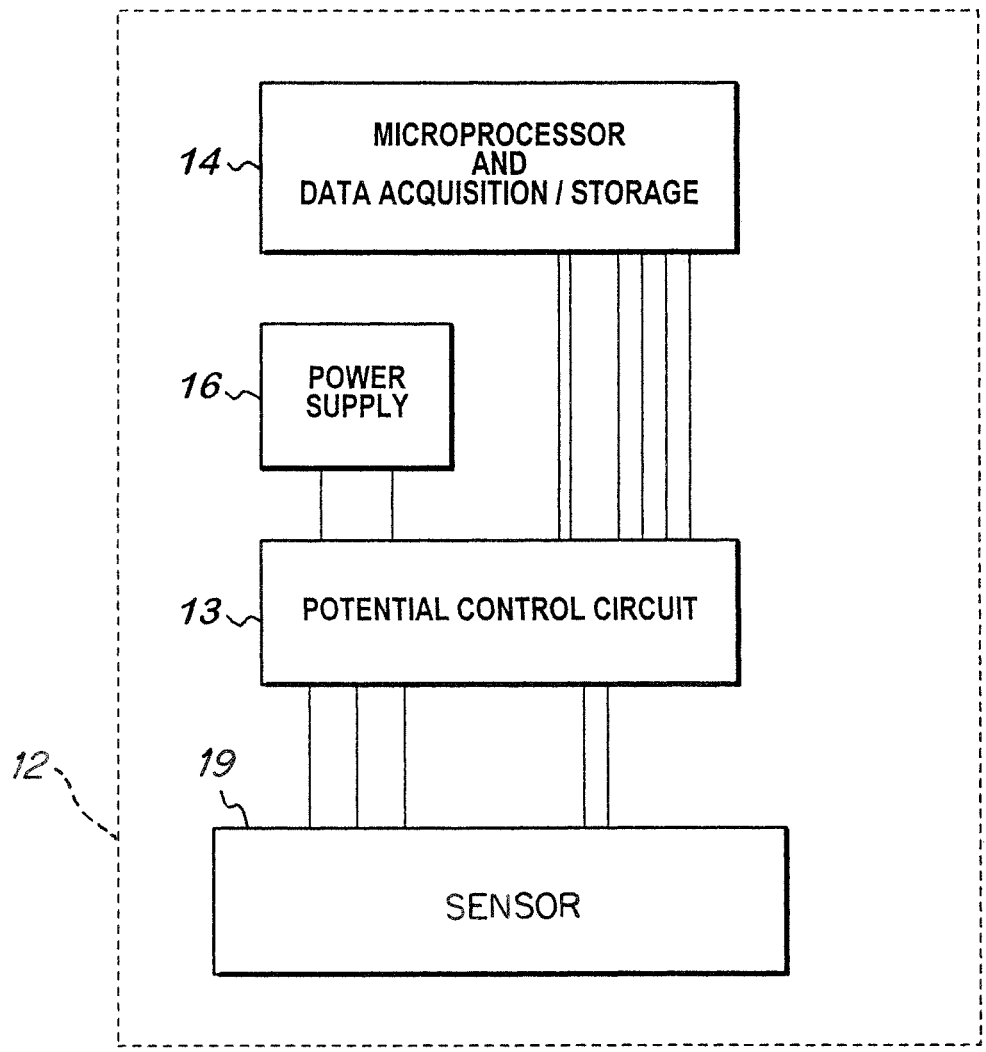
FIG. 9 shows a gas sensor utilized in a gas-sensing instrument.

Referring to FIGS. 8 and 9, a block diagram of the sensor control circuit (13), which can be used with any embodiment of the present invention is shown. The sensor control circuit (13) is designed to: 1) control the potential of the sensing electrode (7) at a predetermined voltage (the "potentiostatic voltage", or "$E_{pot}$"); 2) measure the temperature; 3) convert the gas concentration-related current to a temperature-compensated voltage signal; and 4) provide properly amplified voltage to the data acquisition/storage microprocessor (14). An on-board micro power-regulated power supply (16) uses the microprocessor's (14) power supply to provide the required ±3.9 volts for the sensor circuitry. The DC power can be supplied by a 6-V battery (16d) or an AC adaptor (16e).

The control amplifier portion (17b) of the sensor control circuit (13) consists of a micro power operational amplifier (e.g., MAX407 or LM6062). The sensing (7), counter (5) and reference (4) electrode portions of the sensor assembly (25) are in the feedback loop of the control amplifier (17b) as shown in FIG. 8, a standard configuration for potentiostat circuits. An adjustable voltage divider (17a) allows the polarizing voltage ($E_{pot}$) to be set at a predetermined voltage range such as 0 to 50 mV. This signal is compared to the reference electrode (4) voltage (which appears with it at the summing junction) by the control amplifier (17b) of the sensor control circuit (13). The latter adjusts the current through the sensor cell (10) to minimize the difference between the $E_{pot}$ and the reference electrode (4) voltages.

The resulting sensor cell assembly (19) current (flow of electrons from sensing electrode (7) to counting electrode (5), which is linearly related to the concentration of gas, is transformed into a voltage signal by the current-to-voltage converter (15a). Temperature compensation of the sensor signal is effected in the next stage of amplification (15b) using a thermistor (18a) which is positioned in the gas sensor housing (10). The last stage of amplification (15c) provides the necessary inversion of the voltage signal as well as gain adjustment, to permit calibration for normal variations in sensitivity among sensors. The same type of micro power operational amplifier is used for these stages (15*a*), (15*b*), (15*c*) as for the control amplifier (15*b*). The transformed current signal is directed to an A/D channel on the data acquisition board of the microprocessor (14).

Power for the sensor control circuit (13) is provided by a Duracell 6-V battery (16*d*) (PX28A or 28L) through a micro power-regulated power supply (16). The power supply (16) utilizes a voltage inverter (e.g., ICL 7660) (16*a*) to convert the positive battery voltage to a negative voltage of the same magnitude, and a positive voltage regulator (e.g., MAX663) (16*c*) and negative voltage regulator (e.g., MAX664) (16*b*) to provide a stable ±3.9 volts.

The film type gas or vapor-sensing instrument (12), as shown in FIG. 9, includes the sensor cell assembly (19), potential-control circuitry (13), and the microprocessor (14) with the data acquisition-recording unit. The sensing instrument (12) is preferably battery operated, and has the ability to sample the gas or vapor and temperature signals at intervals and store in the random access memory (RAM) on the data acquisition board days to weeks of data. The data acquisition circuit microprocessor is programmed to sample and store the gas concentration signals at preset intervals. Data are off-loaded to a personal computer by accessing the microprocessor through an RS232 port.

The sensor cell assembly (19) and its potential-control circuit (13) are integrated with a battery-operated microprocessor (14) of 32K memory, which samples the sensor signal as well as temperature and other signals at 10-, 20-, or 30-second intervals and stores an average value at intervals of 2, 5, or 10 minutes according to a programmable protocol. The data acquisition/storage unit in the microprocessor (14) can record 8 days of data, storing at 2-minute intervals, or up to 40 days storing at 10-minute intervals. In clinical testing to date, a 2-minute interval is suitable for one-day clinical studies and a 10-minute interval is appropriate for extended use. The microprocessor (14) with data acquisition/logic circuit can be programmed to sample more than one analog signal from the control circuit (13), and to convert these to digital signals and store them (i.e., gas concentration and temperature) at preset intervals together with real-time data. Data are off-loaded to a personal computer by accessing the microprocessor (14) through an RS232 port. After downloading, the digital data are converted to engineering units of gas concentration and temperature, and can be graphed by a menu-driven Lotus® 123 spreadsheet. Through a potentiometer in the gain amplifier circuit (15*c*), the device can be calibrated with calibrated gas samples, to indicate gas concentrations in the ambient. The potential-control circuit (13) shown in FIG. 8 is powered, in a preferred embodiment, by six 1½-volt AA-size batteries (16*d*). A typical microprocessor (14) with data acquisition-recording capability that has been successfully used is sold by ONSET Computers, Falmouth, Mass., under the product name of "Tattletale Lite®." The sensor cell assembly (19) with its control circuit (13) is also designed to yield a current or voltage signal proportional to gas flux that could be used to continuously transmit the data to a remote receiving device or central monitoring station or unit. It should be known that the embodiment depicted in FIG. 8 is for exemplary purposes and is not a sole limitation of the invention.

The sensing electrodes can be organized in multiple arrays or sets containing a necessary number of counter or reference electrodes. Reference electrodes such as Pt/air ($O_2$), $PtO_2$, or dynamic hydrogen electrode known in the art may be employed. Electrically driven 3- or 2-electrode film type configurations may be employed using potentiostatic, potentiodynamic or potential control. Two-electrode configurations require a reversible or stable counter-reference electrode such as Pt/air ($O_2$), $PtO_2$ or $Pt/H_2$ which has a higher BET (Brunauer, Emmett, Teller) surface area (25 $m^2$/g or larger) and/or larger geometric surface areas than the sensing electrode.

Electrochemically reversible electrodes may be used in 3 or 2 electrode configurations, but especially in a 2-electrode arrangement where the counter electrode also acts as a reference electrode. Electrochemically reversible electrodes are constructed of stable catalyst materials and usually have a relatively large electrochemical active surface area so that they remain stable and their potential is not perturbed by small current flow. Examples include $PtO_2$ and Ag/AgCl electrodes.

Figure 10:
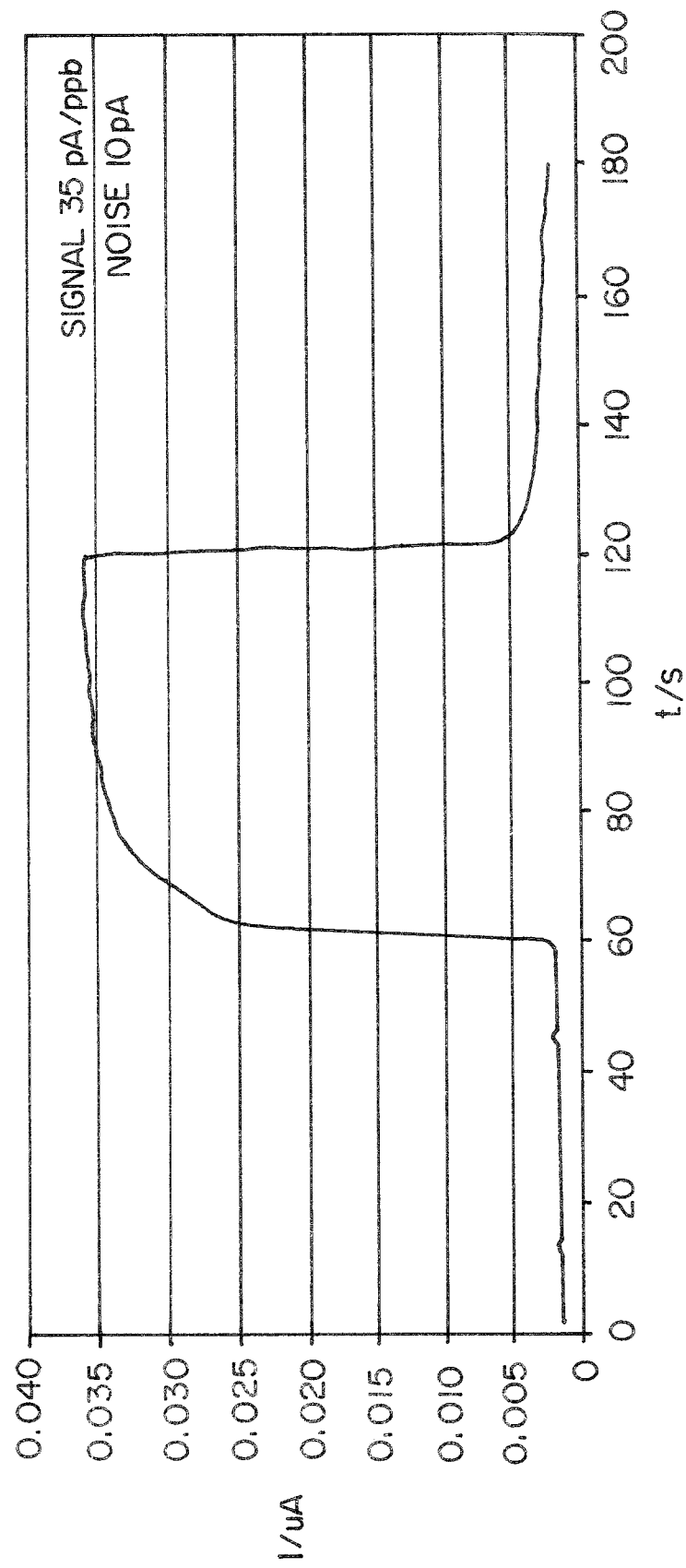
FIG. 10 is a plot of current (μA) vs. time (seconds) illustrating the real time response of a sensor subjected to 1 ppm $H_2S$ after assembly using dry Nafion® in one preferred embodiment.

A real time plot of current (µA) vs. time (seconds) illustrating the response of a sensor subjected to 1 ppm $H_2S$ after assembly using dry Nafion® as shown in FIG. 10, demonstrates that the sensor prepared with dry Nafion® responds within two minutes to 90% of a stable response. The background response signal with air is 10 nanoamps (nA). The response signal with 1 ppm $H_2S$ in air is 35 nA. This corresponds to a net response signal for 1 ppm $H_2S$ in air of 25 nA.

Figure 11:
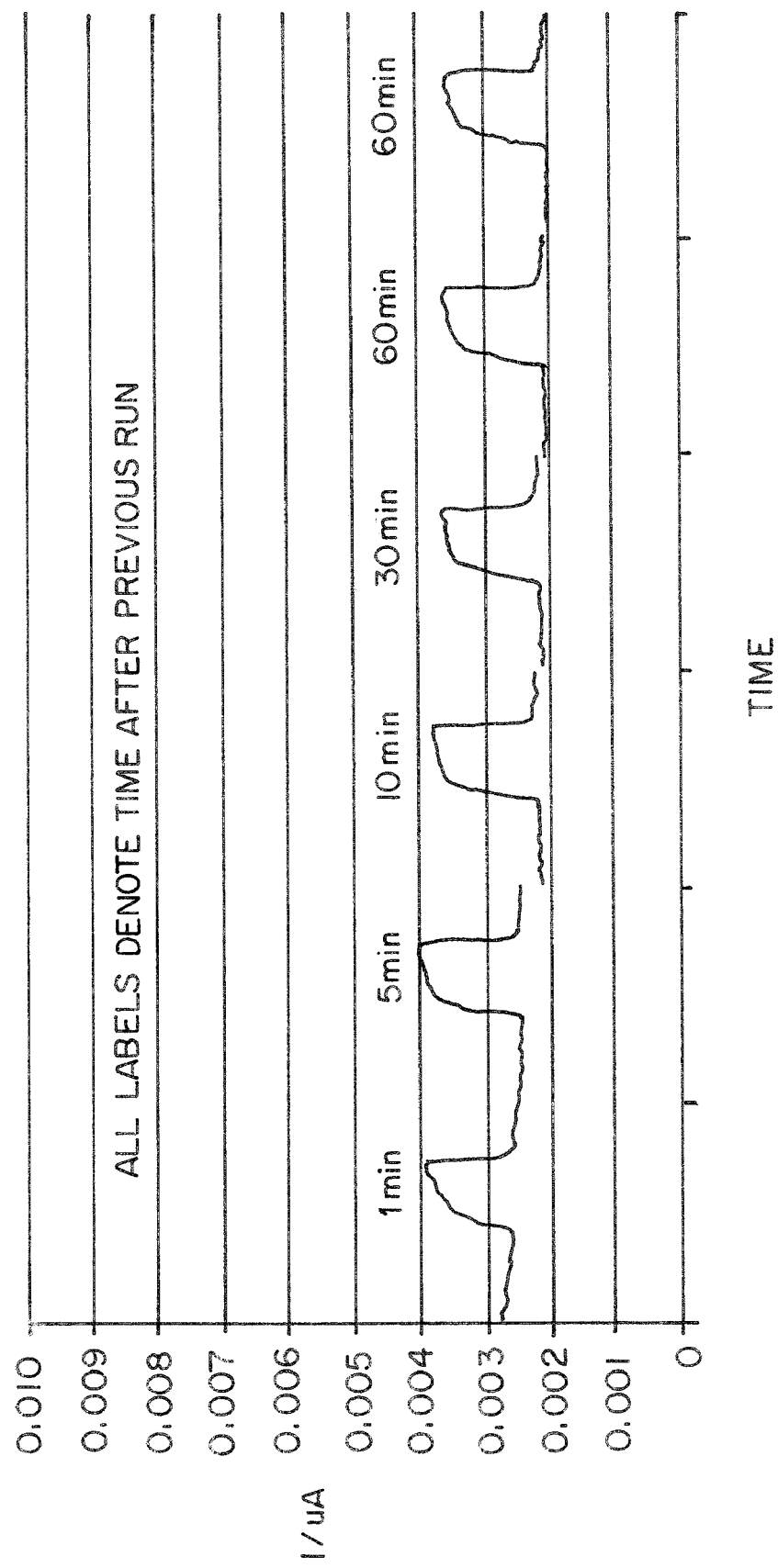
FIG. 11 is a plot of current (μA) vs. time (minutes) illustrating various real time responses and decreased stabilization time for thin film sensors subjected to 100 ppb $H_2S$ after assembly using dry Nafion® in one preferred embodiment.

FIG. 11 shows a plot of current (µA) vs. time (minutes) illustrating various real time responses and decreased stabilization time for thin film sensors subjected to 100 ppb $H_2S$ after assembly using dry Nafion®. The plot demonstrates that the sensor prepared with dry Nafion® responds within two minutes to 90% of a stable response.

Figure 12:
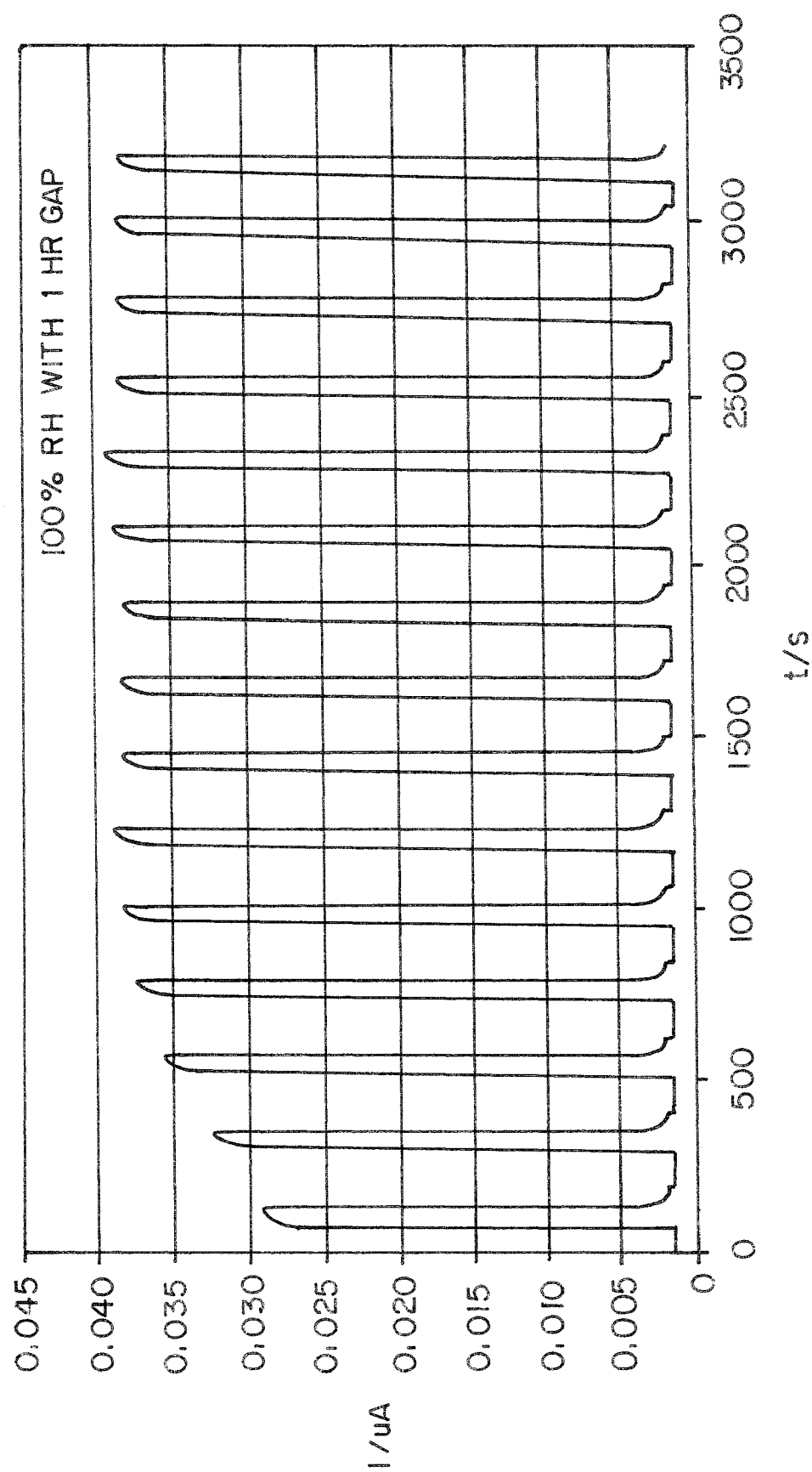
FIG. 12 is a plot of current (μA) vs. time (seconds) illustrating the real time response of a sensor subjected to 1 ppm $H_2S$ at 100% relative humidity after assembly using dry Nafion® and a one-hour storage period in one preferred embodiment.

FIG. 12, is a plot of current (µA) vs. time (seconds) illustrating the real time response of a sensor subjected to 1 ppm $H_2S$ at 100% relative humidity after assembly using dry Nafion® and a one-hour storage period. The graph shows that sensors prepared using dry Nafion® respond to 90% of a stable response, which is reached within a few minutes of assembly.

FIG. 13 is a flow chart illustrating the manufacturing process for sensors of the present invention. The sensors of the present invention are manufactured using known techniques for manufacturing electrochemical sensors, including method of mass-producing film type gas sensors by stacking a number of component layers to form a series of adjacent sensors which are subsequently separated into individual sensors. The component layers are stacked by depositing a second substrate (28) on top of a completely manufactured sensor.

FIG. 13 depicts a method of making an electrochemical sensor for the detection of an analyte (36) in a gas sample (37) by providing (29) a dry ionomer membrane free from liquid droplets; providing (38) a substrate with at least one opening through its surface and a first electrode layer adjacent to the opening; forming (40) at least one opening in the substrate; forming (30) at least one hole in the dry ionomer membrane; connecting (31) the dry ionomer membrane to the substrate; aligning (32) the hole in the dry ionomer membrane with the opening in the substrate for defining (39) a gas passage; and depositing (33) a second electrode on the substrate for operatively connecting the ionomer membrane, the first electrode, the second electrode, and an analyte of interest. The figure also illustrates providing (34) at least one reservoir into the sensor, and the housing of the sensor. The reservoir is filled (35) with a liquid prior to initial use of the sensor. Preferably the liquid used in the reservoir of the present invention is water. FIG. 13 also illustrates the step of optionally depositing (41) an additional electrode on the sensor substrate. The additional electrode can be a reference electrode.

FIG. 13 illustrates the novel step of providing (29) a membrane. In particular the membrane provided is a dry ionomer membrane, which is free from liquid droplets. Although Nafion® is a preferred ionomer for use in such sensors, it is not the only solid electrolyte polymer available. For instance, both anionic and cationic polymer membranes can be incorporated into electrochemical sensors of this type. Similar ionomers that are part of a class of solid polymeric ion exchangers that conduct ions upon exposure to water are available. Known examples include membranes made from polystyrene with fixed negative sites (sulfonate, carboxylate or phosphonate) or fixed positive sites (quaternary ammonium or quaternary phosphonium). Other examples include Neosepta manufactured by the Tokuyama Corporation, Selemion™ of Asahi Glass, Sybron Ionac, Morgane, PCA, RAI, Gor-Tex® in ionic form and others.

As described above, the dry ionomer membranes can also be defined as those ionomer membranes that are hygroscopic. Hygroscopic membranes are those membranes that readily absorb or attract moisture from the air; or membranes having an affinity for moisture. One such example is Nafion® 117 perflourinated membrane manufactured and sold by E. I. du Pont de Nemours and Co.

FIG. 13 also illustrates the step of forming (30) at least one hole in the ionomer membrane. Making the opening in the ionomer membrane can be performed by any method one of ordinary skill in the art would use to make a hole or slit in the membrane. For example, a simple punch apparatus may be used to punch a hole into a dry Nafion® sheet. The diameter of the punch can easily be changed to change the hole size. Preferably the hole would be about 1.0 mm in diameter. A substrate as described above is also provided. Forming (30) one or more openings in the substrate can be performed, as one of ordinary skill in the art would form an opening. The substrate may be punched or cut to contain holes. These holes are typically about the same size as the hole in the ionomer membrane.

The foregoing description of various embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method of making a sensor, comprising the steps of:
   providing a substrate;
   providing at least one opening in the substrate;
   placing an electrode proximate to the at least one opening; and
   contacting a dry ionomer membrane to the substrate and electrode;
   providing at least one hole in the ionomer membrane;
   aligning the at least one hole with the at least one opening for defining a gas passage;
   wherein, the ionomer membrane is dry during the steps of providing the at least one opening in the substrate, placing the electrode proximate to the at least one opening, contacting the dry ionomer membrane to the substrate and electrode, providing the at least one hole in the ionomer membrane, and aligning the at least one hole with the at least one opening.

2. The method of claim 1 further comprising the step of aligning the at least one opening in the substrate with the electrode for defining a gas passage.

3. The method of claim 1 further comprising the step of positioning a polymer layer upon the electrode for slowing inputs of gas moving through the at least one opening onto a surface of the electrode.

4. The method of claim 1 where the step of providing a substrate further includes positioning a counter electrode in contact with the dry ionomer membrane such that upon wetting the dry ionomer membrane the counter electrode provides an electrical connection.

5. The method of claim 1 where the step of providing a substrate further includes positioning a reference electrode in contact with the dry ionomer membrane such that upon wetting the dry ionomer membrane a reference point is created against which the potential of other electrodes can be measured.

6. The method of claim 1 where the step of providing a dry ionomer membrane further includes obtaining a perfluorosulfonic acid membrane.

7. The method of claim 1 further comprising the step of providing a reservoir without liquid in contact with the dry ionomer membrane.

8. The method of claim 7 further comprising the step of filling the reservoir with a liquid for hydrating the ionomer membrane.

9. The method of claim 1 further comprising the step of aligning the at least one hole with the electrode for defining a gas passage.

10. A method of making an electrochemical sensor, comprising the steps of:
    providing a substrate;
    placing an electrode on the substrate;
    contacting a dry ionomer membrane to the substrate and electrode;
    providing a hole in the dry ionomer membrane proximate to the electrode;
    extending an opening in the substrate;
    aligning the hole and the opening with the electrode for defining a gas passage; and
    wherein, the ionomer membrane is dry during the steps of providing the opening in the substrate, placing the electrode, contacting the dry ionomer membrane to the substrate and electrode, providing the hole in the ionomer membrane, and aligning the hole and opening with the electrode for defining a gas passage.

11. The method according to claim 10, further comprising the providing a reservoir without liquid in contact with the dry ionomer membrane.

12. The method according to claim 11, further comprising the step of filling the reservoir with a liquid for hydrating the ionomer membrane.

* * * * *